United States Patent
Koenig et al.

(10) Patent No.: US 6,528,802 B1
(45) Date of Patent: Mar. 4, 2003

(54) METHOD FOR OPTICAL EXCITATION OF FLUOROPHORE MARKED DNA AND RNA

(75) Inventors: Karsten Koenig, Neuengoenna (DE); Karl-Juergen Halbhuber, Isserstedt (DE); Peter Fischer, Jena (DE); Iris Riemann, Neuengoenna (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/806,375
(22) PCT Filed: Jul. 11, 2000
(86) PCT No.: PCT/EP00/06546
§ 371 (c)(1), (2), (4) Date: Jun. 1, 2001
(87) PCT Pub. No.: WO01/09591
PCT Pub. Date: Feb. 8, 2001

(30) Foreign Application Priority Data

Jul. 29, 1999 (DE) .......................... 199 35 766

(51) Int. Cl.[7] ...................... G01N 27/26; G01N 21/64; G01J 3/30
(52) U.S. Cl. .................. 250/459.1; 250/458.1
(58) Field of Search ................ 250/459.1, 458.1, 250/201.2, 201.3, 307, 334.01, 340, 461.1, 461.2; 356/317; 435/6

(56) References Cited

U.S. PATENT DOCUMENTS

| | | | | |
|---|---|---|---|---|
| 5,062,942 A | * | 11/1991 | Kambara et al. | 204/299 |
| 5,171,534 A | * | 12/1992 | Smith et al. | 422/82.05 |
| 5,213,673 A | * | 5/1993 | Fujimiya et al. | 204/299 |
| 5,290,419 A | * | 3/1994 | Kambara et al. | 204/299 |
| 5,784,157 A | * | 7/1998 | Gorfinkel et al. | 356/318 |
| 5,936,731 A | * | 8/1999 | Cabib et al. | 356/346 |
| 6,049,380 A | * | 4/2000 | Goodwin et al. | 356/317 |
| 6,221,602 B1 | * | 4/2001 | Barbera-Guilem et al. | 435/6 |

\* cited by examiner

*Primary Examiner*—Constantine Hannaher
*Assistant Examiner*—Otilia Gabor
(74) *Attorney, Agent, or Firm*—Reed Smith LLP

(57) ABSTRACT

A method for optical excitation of fluorophore-labeled DNA and fluorophore-labeled RNA, particularly of specific localizations of DNA and RNA labeled by fluorescence in situ hybridization (FISH). It is the object of the method to make possible in a simple manner a high-contrast simultaneous excitation of a plurality of FISH fluorophores which have different fluorescence characteristics and are to be detected and displayed three-dimensionally. The excitation and detection of fluorophores at a depth of the biological material greater than 100 micrometers must be ensured. The FISH fluorophores and DNA markers are excited to fluorescence by a multiphoton excitation simultaneously by pulsed and non-pulsed radiation at a single wavelength in the range between 700 nm to 1000 nm, preferably between 760 nm and 820 nm. A total of 20 commercially available FISH fluorophores and DNA markers were tested. Fluorophores which were excited simultaneously by multiphoton excitation were detected in all tested cases.

9 Claims, 3 Drawing Sheets

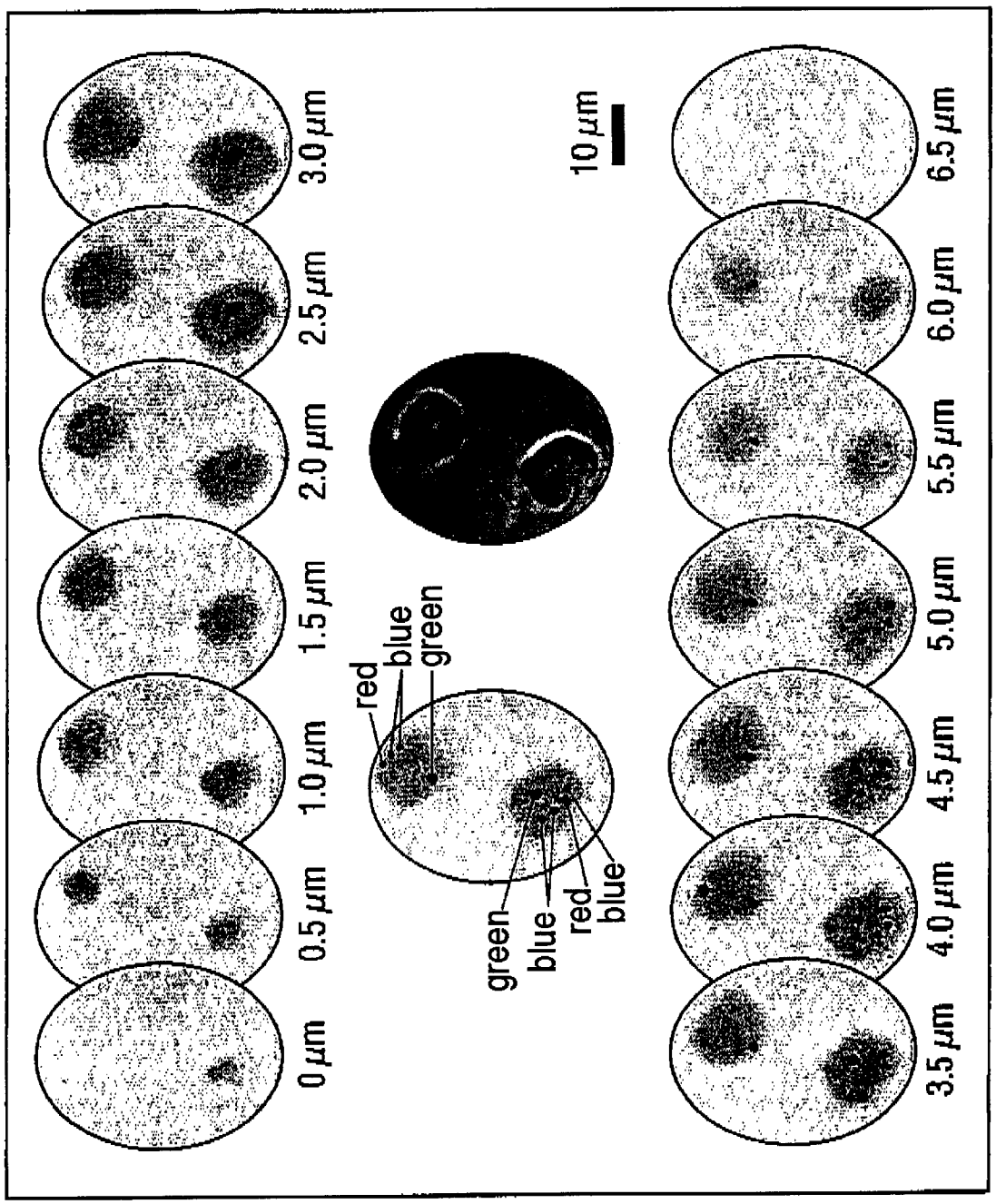

METHOD FOR OPTICAL EXCITATION OF FLUOROPHORE MARKED DNA AND RNA

BACKGROUND OF THE INVENTION a) Field of the Invention

The invention is directed to a method for optical excitation of fluorophore-labeled DNA and fluorophore-labeled RNA, particularly of specific localizations of DNA and RNA labeled by fluorescence in situ hybridization (FISH). The method is suitable for the excitation and spatially-resolved detection of FISH-labeled chromosomal structures and enables simultaneous excitation of a plurality of fluorophores. Therefore, the method is recommended for multigenic detection.

b) Description of the Related Art

There are already known methods for exciting fluorophore-labeled DNA and RNA by means of optical radiation of noncoherent light sources (lamps) or coherent light sources (lasers) and for detecting fluorescence in two or also three dimensions with suitable detectors: (for example, U.S. Pat. Nos. 5,792,610, 5,759,781, DE 196 22 904, DE 4 216 949, Science 273 (1996), 430 and 494, Nature Genet. 12 (1996), 368, Hum. Mol. Genet. 2 (1993), 505, Cytometry 10 (1989), 20 and 11 (1990), 126, Proc. Natl. Acad. Sci. (USA) 89 (1992), 1388). The labeling is carried out on the one hand with nonspecific DNA markers, e.g., DAPI (4,6-diamidino-2-phenylindole hydrochloride) and Hoechst 33342 and on the other hand by specifically-binding fluorophores which enable detection of small gene and chromosome areas as well as entire special chromosomes. The fluorophore is coupled to the desired DNA region by fluorescence in situ hybridization (FISH).

A far-reaching application of the FISH technique is the use of a plurality of fluorophores with different emission behavior for the localization of specific DNA regions which accordingly make possible a multigenic detection through "multicolor detection". This special technique is known as multiplex FISH, M-FISH or multicolor FISH. Different excitation wavelengths are typically used for excitation of the different fluorophores. These excitation wavelengths are provided either by a plurality of different light sources or by light sources with different emission wavelengths. The latter emissions are provided, e.g., by filter wheels with a time offset (not simultaneously) or by special filters with transmission for a plurality of excitation wavelengths (e.g., Dan Pinkel filter) or a multiline output of a laser (e.g., U.S. Pat. No. 5,127,730) simultaneously. For instance, in cytogenetic examination of human chromosomes, the UV emission of a light source, e.g., a high-pressure mercury or xenon lamp, is often used for fluorescence excitation of a nonspecific DNA marker (also known as a counterstain) and blue emission of the light source is used for excitation of a FISH fluorophore with fluorescence in the green range, and green emission of the light source is used for excitation of a FISH fluorophore with fluorescence in the red range. A three-dimensional (3D) representation with high spatial resolution is not possible with these noncoherent excitation sources.

The use of different excitation wavelengths causes considerable problems due to chromatic aberration of the optics (different focal lengths), the necessity of UV optics and the complicated separation of excitation photons and fluorescence photons in case of simultaneous excitation. With simultaneous excitation, problems arise with beam alignment and as a result of costly switching devices, e.g., in the operation of switchable filter wheels.

All of the known methods of this type for optical excitation and detection of specific localizations of DNA and RNA which are labeled by fluorescence in situ hybridization (FISH) are based on a linear excitation or single-photon excitation. With single-photon excitation, fluorescence is induced by photons possessing sufficient photon energy to change the fluorophore to a high-energy electronic state. Fluorescence takes place as a result of the radiating transition in the ground state of the fluorophore. In single-photon excitation, the excitation wavelength is always less than the fluorescence wavelength. Fluorescence excitation is carried out within the total probe area affected by the fluorescence excitation radiation. Accordingly, destruction of probes and fluorophores takes place also outside of the focus volume. Confocal laser scanning microscopes were used heretofore in order to achieve a high-resolution 3D fluorescence image of FISH fluorophores and made it possible to detect the fluorescence signal from different probe depths through the use of pinhole diaphragms. Here, also, there arises the problem of probe destruction and fluorophore destruction outside the detection plane due to the large excitation volume. Three-dimensionally resolved M-FISH technique with the conventional confocal laser scanning microscope is possible only to a very limited extent if at all, because generally only a very few excitation wavelengths are available. Typically, 3D pictures are made with blue/green excitation wavelengths of the argon ion laser at 488 nm and 514 nm and with wavelengths 536 nm and 633 nm of the He-Ne laser. Laser scanning microscopes of the type mentioned above do not usually have an additional UV light source for 3D excitation of the Hoechst and DAPI nonspecific DNA markers.

Therefore, the previous M-FISH method which is based on single-photon excitations has the following disadvantages:

1. The use of a plurality of excitation wavelengths, including ultraviolet radiation of a plurality of light sources or multiline/multiband output of a light source with simultaneous or non-simultaneous fluorophore excitation and consequent problems due to chromatic aberration;

2. no possibility or very limited possibility of 3D display with high spatial resolution;

3. considerable filter problems, especially with simultaneous excitation of a plurality of fluorophores with different excitation wavelengths;

4. low penetration depth of fluorophore excitation radiation, especially UV radiation;

5. large excitation volume and consequent processes of wide-area fluorophore destruction due to photobleaching and photodestruction and possible wide-area destruction of biological specimen; and 6. background fluorescence and consequent considerable contrast problems.

Further, multiphoton excitation is known, per se, and was already predicted in 1931 by Göppert-Meyer (Ann. Phys. 9 (1931)273) and first realized in 1961. For multiphoton excitation of biological probes, radiation in the near infrared (NIR) spectral region is preferably used because there are only a few efficient cell-specific absorbers in this range, so that thermal or photochemical damage due to linear absorption can be virtually ruled out.

Multiphoton excitations with NIR excitation radiation typically require light intensities of more than 100 MW/cm$^2$. Such high intensities can be achieved by means of continuously emitting (cw) lasers or pulsed lasers preferably in the picosecond range and femtosecond range of moderate laser output through high focusing, e.g., by diffraction-limited focusing with objectives having a high numerical aperture (e.g., *Science* 248 (1990), 73–76; *Nature* 377 (1995), 20–21; *J. Microsc.* 1 (1998), 28). U.S. Pat. No. 5,034,613 and the periodical *Science* 248 (1990), 73–76, disclose a two-photon microscope for fluorescence detection and for photo-induced liberation of materials using lasers with pulse widths in the subpicosecond range. Nonlinear excitation of DNA fluorescence dyes DAPI and Hoechst, for example, were demonstrated with multiphoton microscopes (Gryczynski et al., *Bioimaging* 4 (1996), 138–148). However, application of multiphoton excitation for examination of FISH fluorophores and for realizing a multiplex FISH display is not yet known.

OBJECT AND SUMMARY OF THE INVENTION

It is the primary object of the invention to provide a method which makes possible in a simple manner a high-contrast simultaneous excitation of a plurality of FISH fluorophores which have different fluorescence characteristics and are to be detected and displayed three-dimensionally, and which ensures the excitation and detection of fluorophores at a depth of the biological material greater than 100 micrometers and which does not have the above-mentioned disadvantages of the previous methods.

According to the invention, the FISH fluorophores and the nonspecific DNA markers are excited by excitation beams of only one wavelength in the range of 700 nm to 1000 nm, wherein the radiation can be pulsed or not pulsed and the light intensity in a spatially confined volume is greater than 100 MW/cm$^2$.

Surprisingly, it was found that a plurality of common FISH fluorophores and nonspecific DNA markers can also be excited simultaneously by high-intensity near infrared laser radiation of a single suitable wavelength, although in the single-photon excitation spectrum no absorption bands occur at the excitation wavelength and there exist considerable differences in the absorption behavior of the individual fluorophores with different absorption bands in the ultraviolet and visible range. Accordingly, it has been shown that twenty commercially available FISH fluorophores and nonspecific DNA markers could be excited to fluorescence efficiently and with high contrast, including the possibility of three-dimensional representation, with pulsed laser radiation of a wavelength of 770 nm, a pulse duration of 200 fs, a pulse repetition frequency of 76 MHz and a light intensity of about 500 GW/cm$^2$. The fluorescence maximum varied within a range of 480 nm to 650 nm and was accordingly at a distance of at least 150 nm from the excitation wavelength. The separation of excitation photons and fluorescence photons therefore causes no problems and was realized through the use of a simple short-pass filter, e.g., which only transmits radiation of less than 700 nm. The fluorophores were bound to human chromosomes.

In contrast to conventional FISH methods, the light excitation with the intensive laser beam in the near infrared range is based on multiphoton excitation in which two photons (two-photon excitation) or three photons (three-photon excitation) are absorbed simultaneously and every photon provides only a fraction of the energy necessary for a transition to the excited electronic state (see FIG. 1).

A multiphoton excitation of this kind in which two photons (two-photon excitation) or three photons (three-photon excitation) are absorbed simultaneously and every photon provides only a fraction of the energy necessary for a transition to the excited electronic state (see FIG. 1) is not known in technical circles for the examination of FISH fluorophores and DNA markers and for the realization of a novel multiplex FISH display.

Through the use of a laser scanning microscope with a phase contrast objective with a high numerical aperture (63×, 1.25) and motor driven depth adjustment of the probe, the inventors were able, with the laser beam at 770 nm and at 800 nm, to produce three-dimensional multiplex FISH recordings of human fluorescence-labeled chromosomes after multiple FISH labeling with a lateral resolution of less than 500 nm and an axial resolution of less than 1000 nm without using pinhole diaphragms. The probe was raster scanned by the high-intensity laser beam. The different fluorescences excited by the near infrared laser beam were shown simultaneously using corresponding dichroic mirrors and broad-band filters and different detectors. Initial detection of FISH fluorophores and subsequent labeling and detection of DNA with the DAPI fluorophore were also carried out in part.

In the following, the invention will be explained more filly with reference to embodiment examples shown in the drawings.

BRIEF DESCRIPTION OF THE DRAWINGS

In the drawings:

FIG. 3 shows depth-resolved optical slices through fourfold-dyed cell cores of two amniotic fluid cells excited to fluorescence in the NIR.

DESCRIPTION OF THE PREFERRED EMBODIMENTS

Figure 1:
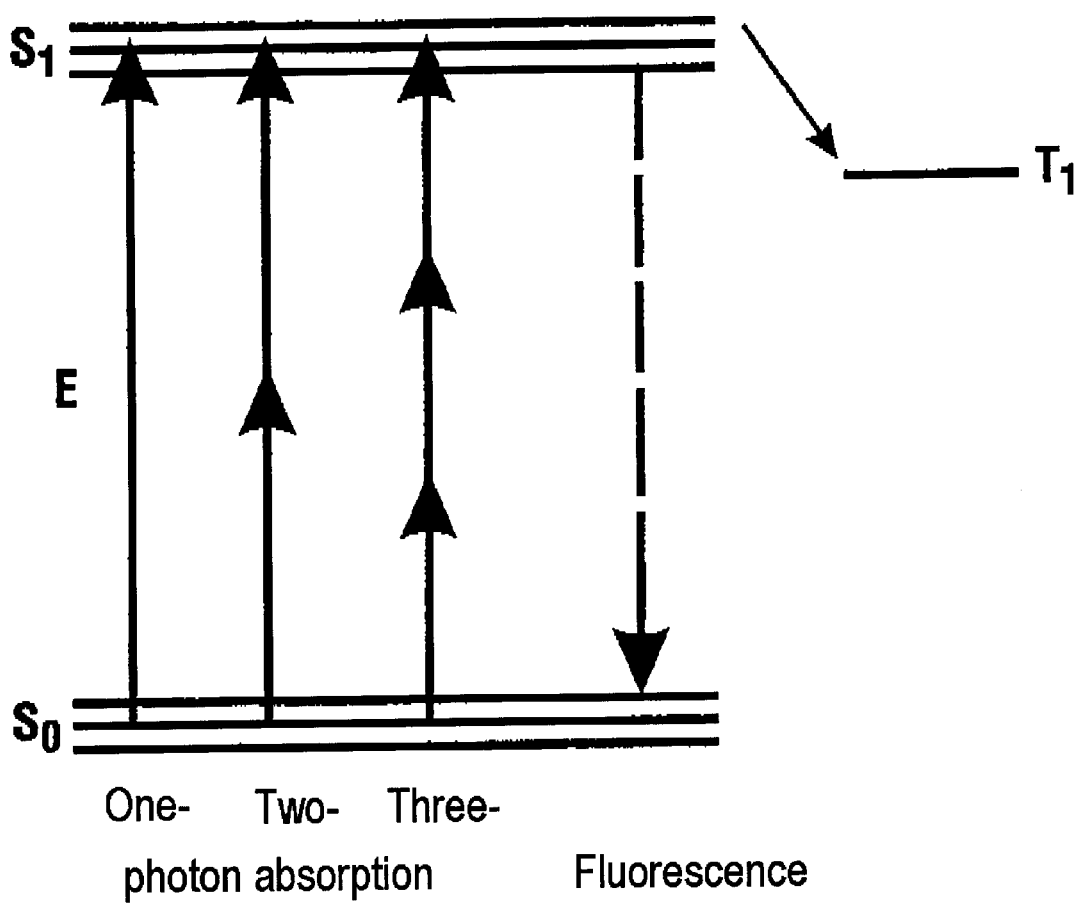
FIG. 1 is a schematic depiction of 1-, 2- and 3-photon absorption.

FIG. 1 shows the operating principle of multiphoton-excited visible fluorescence with intensive near infrared laser radiation compared with single-photon excitation. Two or three photons are absorbed simultaneously and together supply the energy necessary to occupy the required high-energy state from which the fluorescence emission proceeds.

Figure 2:
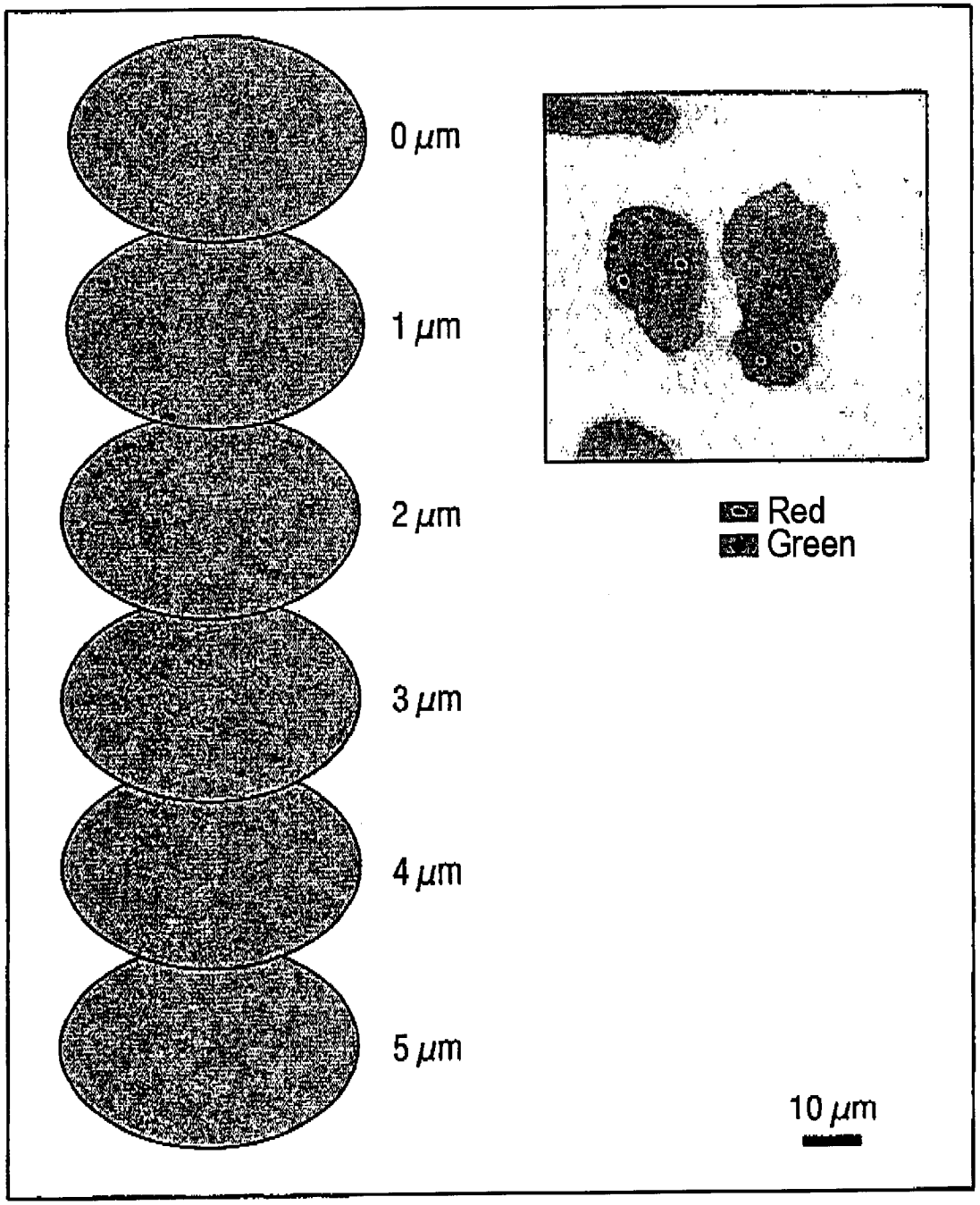
FIG. 2 shows threefold-fluorophore-labeled amniotic fluid cell with fluorescence excitation according to the invention.

FIG. 2 shows depth-resolved recordings of a triple-fluorophore labeled amniotic fluid cell which was irradiated for fluorescence by NIR radiation at a wavelength of 770 nm. The nonspecific DNA marker DAPI and the FISH fluorophores rhodamine (centromere of chromosome 18 labeled) and FITC (centromere of chromosome 8 labeled) were excited to visible fluorescence by two-photon excitation, mentioned above. In this case, the occurrence of three rhodamine hybridization signals in the amniotic fluid cell under examination indicates genetic damage in the form of trisomy 18. The centromeres of chromosomes 8 and 18 do not lie in a plane, but can be localized by the possibility of 3D display in the form of depth-resolved optical slices with an axial distance of 1 m.

FIG. 3 shows depth-resolved optical slices of a fourfold dyeing of cell cores of two amniotic fluid cells with the FISH fluorophores Spectrum Aqua (centromere of chromosome 18 labeled), Spectrum Green (centromere of X-chromosome labeled) and Spectrum Orange (centromere of Y-chromosome labeled) and the nonspecific DNA marker DAPI using 800-nm excitation radiation. In the single-photon absorption spectrum and in the fluorescence spectrum, Spectrum Aqua has bands at 433 nm and 480 nm, Spectrum Green has bands at 509 nm and 538 nm, Spectrum Orange has bands at 559 nm and 588 nm, and DAPI has bands at 358 nm and 561 nm. The fluorescence pictures of the cores shown in FIG. 3 show red- and green-fluorescing FISH signals indicating a female embryo. In addition, one of the cores has three blue-fluorescing signals indicating a trisomy 18. The recordings which were made in different planes of the cell core at an axial distance of 0.5 m show the spatial arrangement of the cell cores with reference to the DAPI fluorescence and the spatial position of the FISH-labeled centromeres in the cell cores having a size of about 10 m.

While the foregoing description and drawings represent the present invention, it will be obvious to those skilled in the art that various changes may be made therein without departing from the true spirit and scope of the present invention

What is claimed is:

1. A method for optical excitation of fluorophore-labeled DNA and RNA in which a plurality of fluorophores with different fluorescence spectra which are to be detected are excited by radiation to fluorescence in the visible spectral range, said method comprising the step of exciting the fluorophores simultaneously by radiation of a single wavelength in a range of 700 nm to 1000 nm to induce multi-photon fluorescence excitation of the fluorophores.

2. The method according to claim 1, wherein the step of exciting the fluorophores is carried out with radiation of a wavelength between 730 nm and 820 nm.

3. The method according to claim 1, wherein the radiation for the multi-photon fluorescence excitation has an intensity of at least 100 MW/cm$^2$ and at most 100 TW/cm$^2$ by focusing in a spatially confined volume.

4. The method according to claim 1, wherein the step of exciting the fluorophores is carried out with radiation that is not pulsed.

5. The method according to claim 1, wherein the step of exciting the fluorophores is carried out with pulsed radiation.

6. A method for optical excitation of fluorophore-labeled DNA and RNA comprising the step of exciting a plurality of fluorophores with different fluorescence spectra simultaneously by radiation of a single wavelength in a range of 700 nm to 1000 nm to induce multi-photon fluorescence excitation of the fluorophores.

7. A method of observing samples using a multi-color fluorescence in situ hybridization technique, the method comprising:

labeling DNA and RNA of a sample with a plurality of fluorophores having different fluorescence spectra;

applying radiation of a single wavelength in a range of 700 nm to 1000 nm to the sample to induce multi-photon excitation of the fluorophores contained in the sample; and detecting fluorescences of the plurality of excited fluorophores.

8. The method according to claim 7, wherein the step of applying radiation includes applying radiation of a single wavelength in a range between 730 nm and 820 nm.

9. The method according to claim 7, wherein the step of applying radiation includes applying a pulsed radiation having an intensity of at least 100 MW/cm$^2$ and at most 100 TW/cm$^2$ by focusing in a spatially confined volume.

* * * * *